Figure 1:
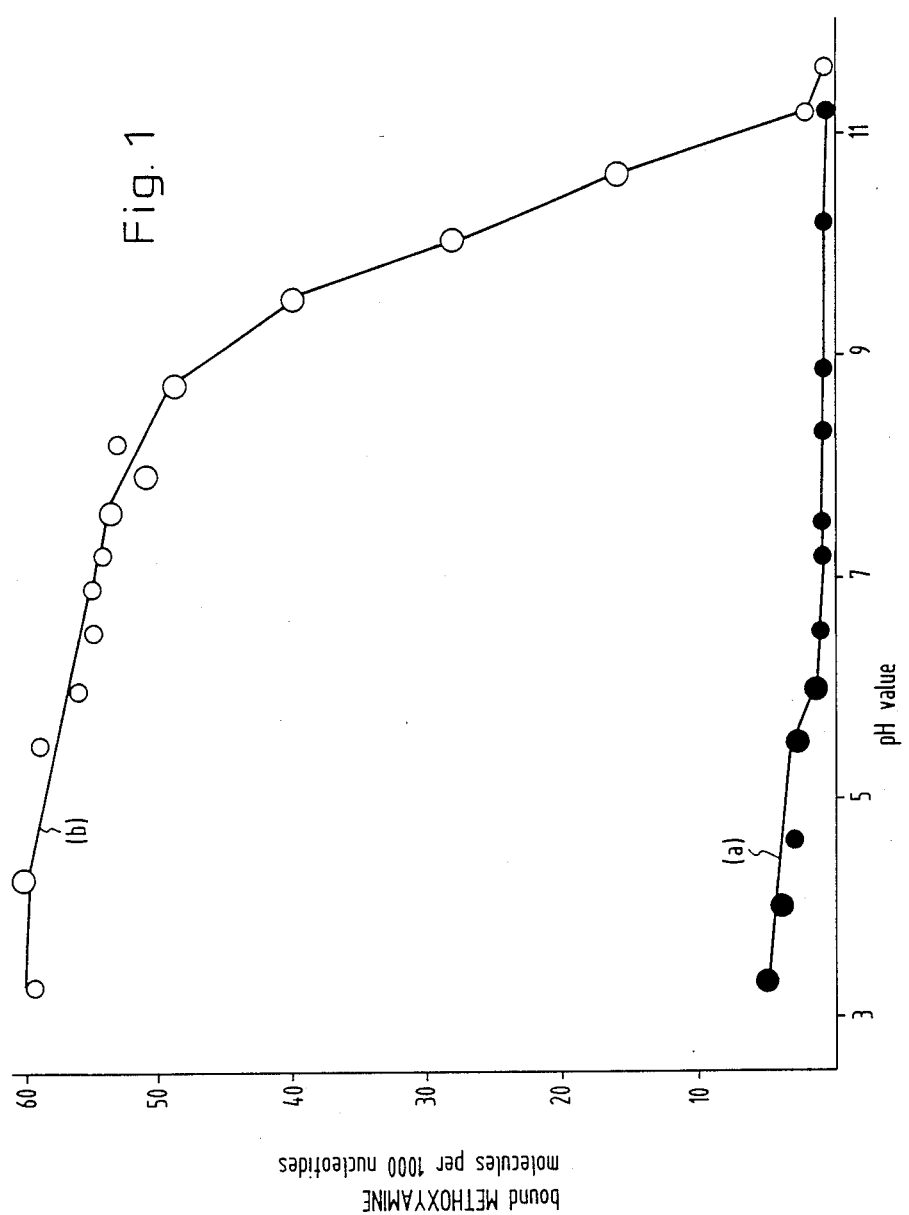

United States Patent [19]

Talpaert-Borle et al.

[11] Patent Number: 4,863,847
[45] Date of Patent: Sep. 5, 1989

[54] PROCESS FOR DIRECTLY DETERMINING APURINIC AND APYRIMIDINIC SITES IN DNA

[75] Inventors: Myriam Talpaert-Borle, Ispra, Italy; Michel Liuzzi, Wiltz, Luxembourg

[73] Assignee: Europaische Atomgemeinschaft, Italy

[21] Appl. No.: 592,427

[22] Filed: Mar. 22, 1984

[30] Foreign Application Priority Data

Mar. 23, 1983 [DE] Fed. Rep. of Germany ....... 3310563
Apr. 27, 1983 [DE] Fed. Rep. of Germany ....... 3315116

[51] Int. Cl.$^4$ .......................... C12Q 1/68; C12Q 1/34
[52] U.S. Cl. .......................... 435/6; 435/18; 436/94
[58] Field of Search .......................... 435/6, 29, 15, 18; 436/94

[56] References Cited

PUBLICATIONS

Coombs et al, Biochim. Biophys. Acta, 174: 161–173 (1969).
Talpaert-Borle et al, Biochim. Biophys. Acta, 740: 410–416 (Sep. 9, 1983).
Talpaert-Borle et al, J. Biol. Chem., 257(3): 1208–1214 (1982).
Talpaert-Borle et al, J. Biol. Chem., 254(14): 6387–6391 (1979).
J. of Virology, 40(1): 204–210 (1981), H. Warner et al., "Evidence that the UV Endonuclease Activity Induced by Bacteriophage T4 Contains Both Pyrimidine Dimer DNA, Glycosylase and Apyrimidinic/Apurinic Endonuclease Activities in the Enzyme Molecule".
Proc. Natl. Acad. Sci. USA., 78(5): 2742–2746 (1981), Y. Nakabeppu et al., "Physical Association of Pyrimidine Dimer DNA Glycosylase and Apurinic/Apyrimidinic DNA".

*Primary Examiner*—Esther M. Kepplinger
*Attorney, Agent, or Firm*—Scully, Scott Murphy & Presser

[57] ABSTRACT

A simple and fast process is described which serves to directly determine apurinic and apyrimidinic sites (AP sites) in DNA using [$^{14}$C]methoxyamine which, after loss of a purine or pyrimidine base, respectively, reacts with the resultant aldehyde groups of the deoxyribose groups.

The incorporation of the [$^{14}$C]methoxyamine in DNA is proportional to the number of AP sites. Since methoxyamine does not cause the DNA to degrade, the unreacted AP sites can be measured in order to determine the radioactivity of the acid-insoluble fraction.

The process lends itself to the analysis of DNA-damages such as those which are physically or chemically produced. Moreover it is suitable to demonstrate and determine the activity of DNA glycosylases, in particular of uracil-DNA glycosylases.

7 Claims, 6 Drawing Sheets

PROCESS FOR DIRECTLY DETERMINING APURINIC AND APYRIMIDINIC SITES IN DNA

Apurinic and apyrimidinic sites (AP sites) in DNA are defects which can be produced in different ways; see T. Lindahl and S. Ljungquist, Molecular Mechanisms for Repair of DNA, publishers P. C. Hanawalt and R. B. Setlow, Part A, pages 31-38, Plenum Press, New York, 1975, and T. Lindahl, Progress in Nucleic Acids Research and Molecular Biology, publishers W. E. Cohn, Vol. 22 (1979), pages 135-192, Academic Press, New York. AP sites may form even at normal pH by spontaneous hydrolysis of the sugar bond between the deoxyribose group and the purine base or pyrimidine base. Moreover, AP sites appear after modification of the bases which weaken the glycosyl bond, for instance alkylation of the purines, saturation of the $C_5$-$C_6$ bond of the pyrimidines and fragmentation of the heterocyclic ring. Moreover, a part of the damaged bases can also be removed by specific DNA glycosylases. Finally, AP sites in DNA can also be produced by some antitumor-antibiotics, such as Bleomycin; see W. E. G. Müller and R. K. Zahn Progress in Nucleic Acids Research and Molecular Biology; Publishers W. E. Cohn, Vol. 20 (1977), pages 21-57, Academic Press, New York.

AP sites are serious DNA defects. They may cause mutations; see R. M. Schaaper, B. W. Glickman and L. A. Loeb, Cancer Research, Vol. 42 (1982), page 3480-3485 and R. M. Schaaper, B. W. Glickman and L. A. Loeb, Mutation Research, Vol. 106 (1982), pages 1-9. AP sites are non-coding defects.

So far, only intact AP sites have been determined, the determination was effected in an indirect manner. The assay is based on the determination of strand breaks (nicks) after chemical or enzymatic cleavage of a phosphodiester bond adjacent to the AP site.

Moreover, it is known that apurinic acid, that is the purine-free DNA derivative obtained after treating DNA with dilute mineral acid, can be reacted with aldehyde-reagents, such as hydroxylamine, semicarbazide, phenyl hydrazine or [$^{14}$C]methoxyamine; see N. M. Coombs and D. C. Livingston, Biochim. Biophys. Acta, Vol. 174 (1969), pages 161-173, in particular page 172.

The different known methods for determining the AP sites in DNA have several disadvantages. Some methods are time-consuming and labor-intensive, other methods are not sufficiently sensitive. Finally, there are methods which are restricted to a limited number of AP sites. Moreover, all methods require two steps (breaking of the DNA and analysis of the breaks) and only determine intact AP sites.

Consequently, it is the object of the invention to develop a process for directly determining all AP sites, be they intact or associated with strand breaks, the process being based on the reaction of the aldehyde group(s) of the deoxyribose group(s) with [$^{14}$C]methoxyamine, said aldehyde groups being formed after a purine or pyrimidine loss.

The subject matter of the invention thus is a process for directly determining apurinic and apyrimidinic sites (AP sites) in DNA, the process being characterized in that the DNA-sample to be examined is reacted with a specific excess amount of [$^{14}$C]methoxyamine for a sufficiently long time at a pH-value of about 6.8 to 7.4, the unreacted [$^{14}$C]methoxyamine is subsequently separated in acid medium and the radioactivity of the DNA[$^{14}$C]methoxyamine reaction product is determined.

The process of the invention also lends itself to the determination of DNA glycosylases, in particular of Uracil-DNA glycosylases. In this case, a DNA-sample can be reacted under the above-specified conditions with a specific excess amount of [$^{14}$C]methoxyamine and with the DNA glycosylase to be determined, since the DNA glycosylase activity is not influenced by [$^{14}$C]methoxyamine. The AP sites formed by the DNA glycosylase react with [$^{14}$C]methoxyamine and are determined in the manner described above.

When a polydeoxyribonucleotide containing uracil is incubated with a uracil-DNA glycosylase, a number of methoxyamine-reactive sites which is proportional to the amount of the enzyme and the incubation period is formed in the DNA. These sites are approximately equal to the amount of liberated uracil.

The reaction is preferably carried out with [$^{14}$C]methoxyamine at pH 7.2 and at 37° C.

The process according to the invention is fast, simple and sensitive. It requires neither the use of DNA having a specific configuration nor specific processes of analysis. The process is suitable as routine method for determining DNA defects and for determining reagents which modify the DNA, for instance cancerogenic or mutagenic substances.

LEGENDS FOR THE FIGURES

FIG. 1: Influence of the pH value on the reaction of [$^{14}$C]methoxyamine with alkylated-depurinated DNA The reaction mixtures contain 200 μg/ml of either untreated (curve a) or alkylated depurinated DNA (curve b). The reaction mixtures are incubated with 5 mM [$^{14}$C]methoxyamine (end concentration) for 30 minutes at 37° C. The pH values indicated are obtained after extensive dialysis against 10 mM NaCl, 10 mM potassium phosphate at different pH values or after addition of hydrochloric acid or sodium hydroxide solution. The incorporation of [$^{14}$C]methoxyamine in DNA is determined in the manner described above.

Figure 2:
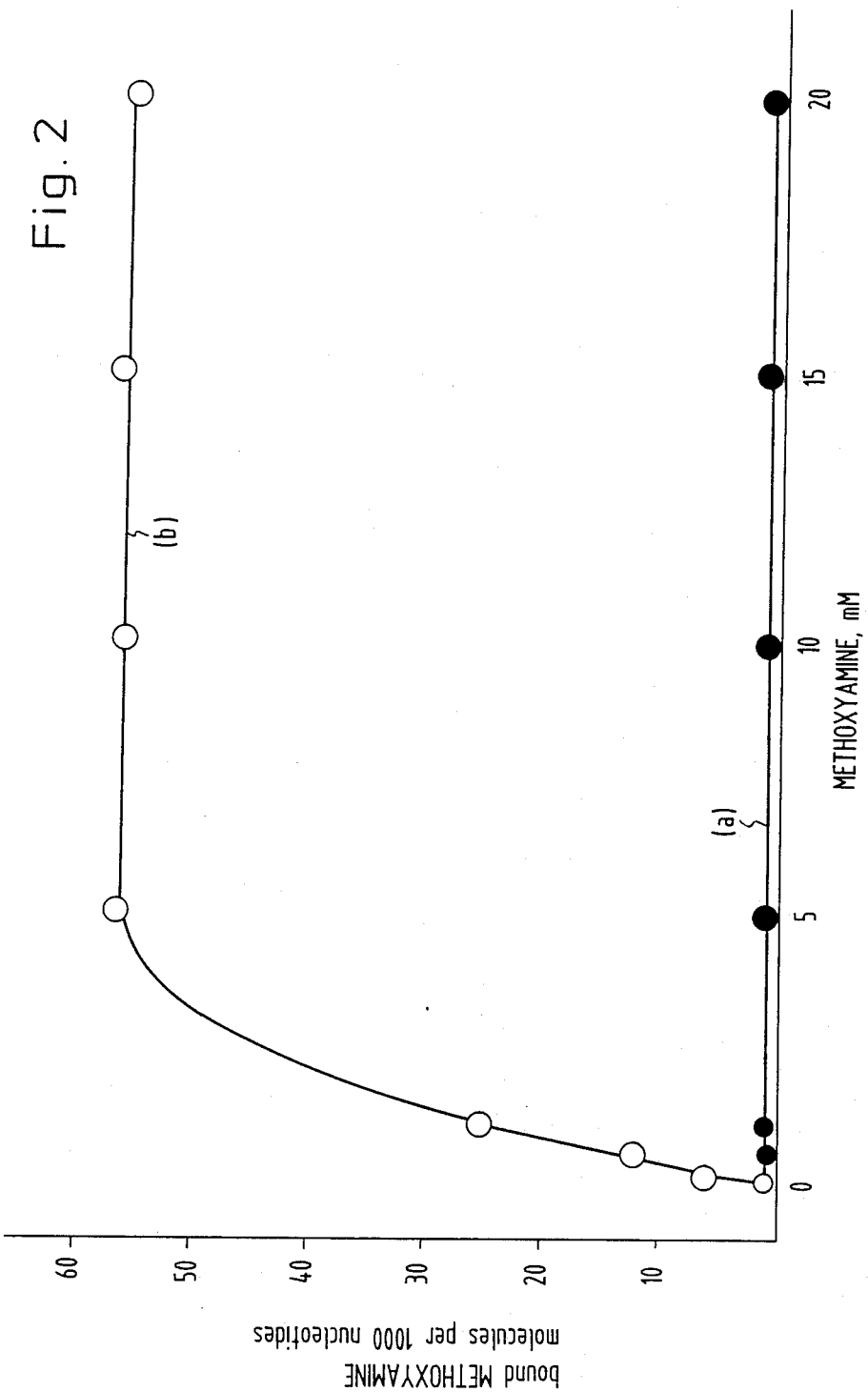

FIG. 2: Incorporation of [$^{14}$C]methoxyamine in alkylated-depurinated DNA as a function of the reagent concentration The reaction mixtures contain 200 mg/ml of either untreated or alkylated-depurinated DNA in 0.1M borate buffer, pH 7.2. They are incubated at 37° C. for 30 minutes with the indicated concentrations of [$^{14}$C]methoxyamine. The [$^{14}$C]methoxyamine quantities bound to untreated (curve a) and to alkylated-depurinated DNA (curve b) were determined in the manner described above, after previous precipitation with hydrochloric acid.

Figure 3:
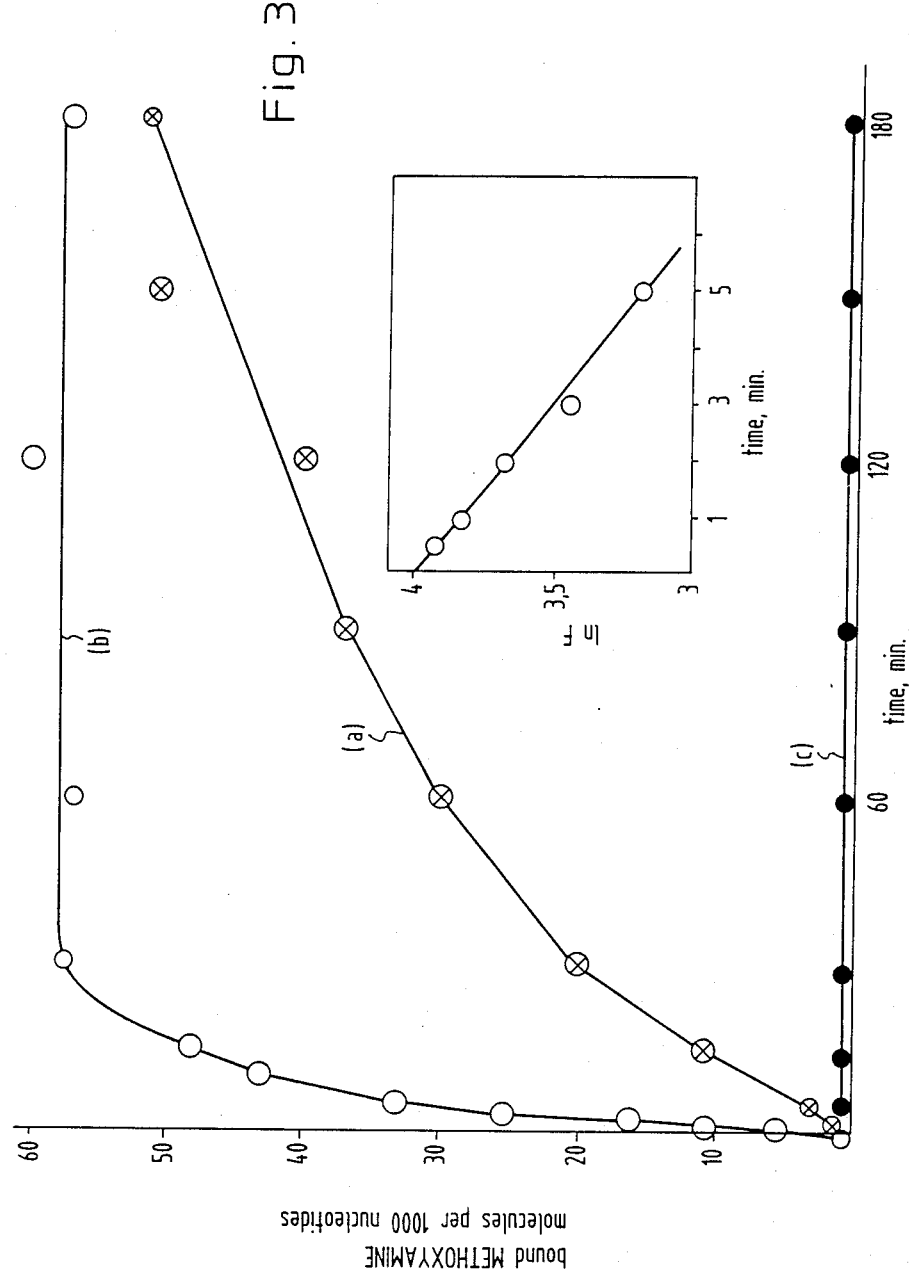

FIG. 3: Incorporation of [$^{14}$C]methoxyamine in alkylated, depurinated DNA as a function of time The reaction mixtures contain 200 μg/ml of either untreated or alkylated-depurinated DNA. Incubation was performed at 37° C. and pH 7.2 with 1 mM (curve a) or 5 mM (curve b) [$^{14}$C]methoxyamine for the alkylated-depurinated DNA and with 5 mM (curve c) for the untreated DNA. At the indicated times, the incorporation of [$^{14}$C]methoxyamine in DNA is determined in the manner described above.

Insert of FIG. 3:

The number of unreacted sites (F) as a function of time.

The number of unreacted sites (F) is calculated by substracting the number of the reacted sites from the number of total sites. Both are computed from the amount of incorporated [$^{14}$C]methoxyamine. The graph represents the variation of lnF with time.

Figure 4:
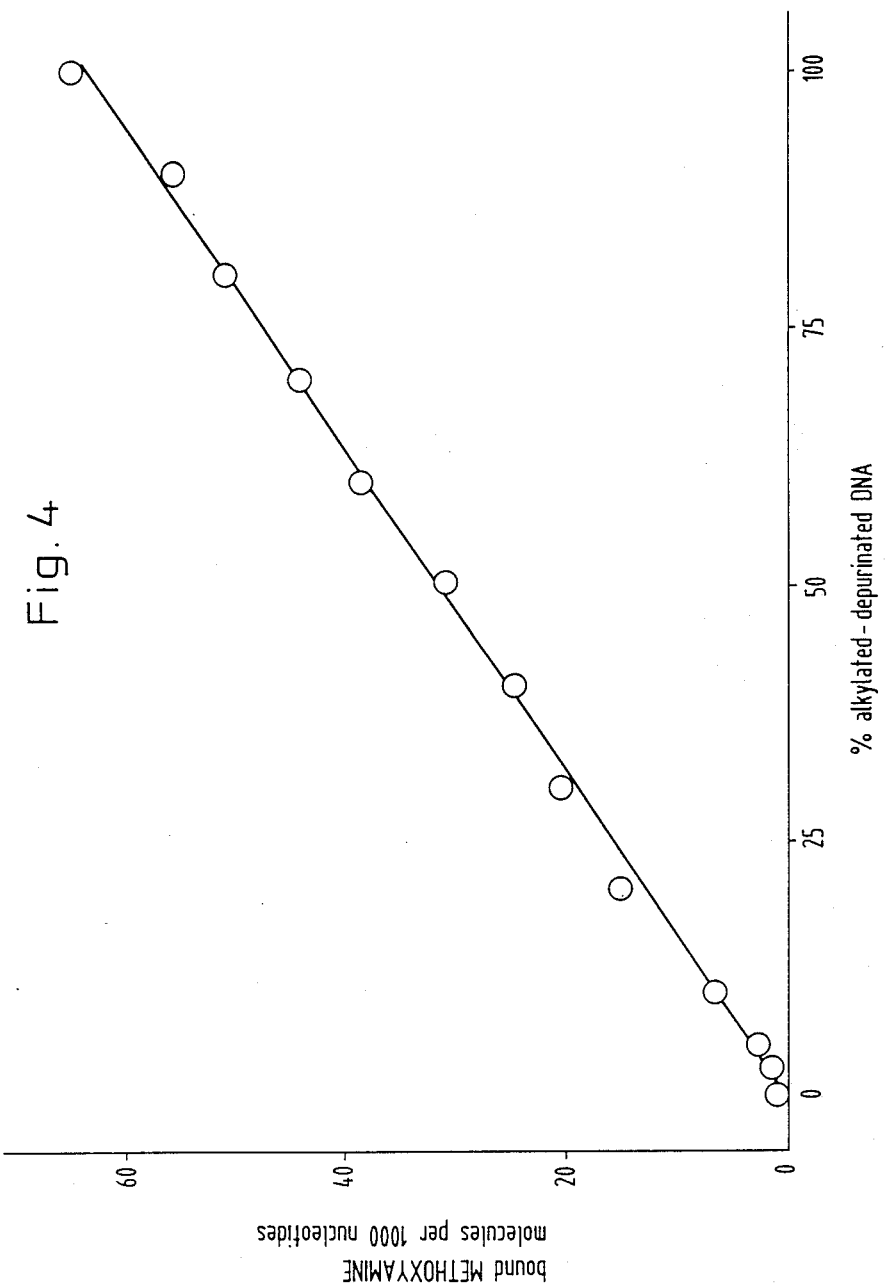

FIG. 4: Incorporation of [$^{14}$C]methoxyamine as a function of the reactive sites in alkylated-depurinated DNA The reaction mixtures contain different amounts of reactive sites which are obtained by mixing different amounts of untreated and alkylated-depurinated DNA at a concentration of 115 μg/ml. The reactions are performed under standard conditions, i.e. 5 mM [$^{14}$C]methoxyamine, 0.1M borate buffer, pH 7.2, at 37° C. for 30 minutes. The incorporation of [$^{14}$C]methoxyamine in DNA is determined in the manner described above.

Figure 5:
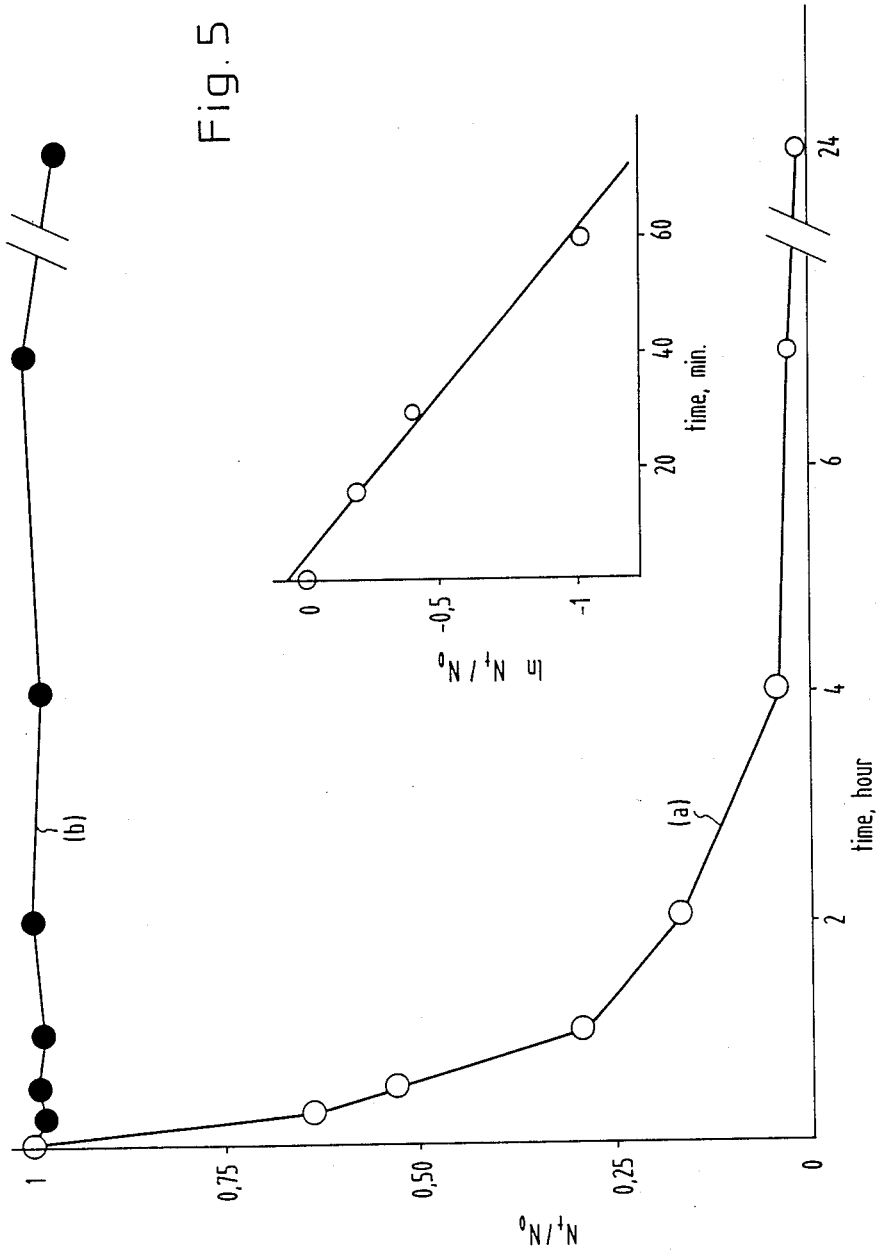

FIG. 5: Stability of the complex or the compound resulting from the reaction of methoxyamine with alkylated-depurinated DNA Alkylated-depurinated DNA (200 μg/ml) is incubated with [$^{14}$C]methoxylamine under the standard conditions. Unreacted excess reagent is separated by extensive dialysis against 10 mM NaCl, 10 mM potassium phosphate, pH 7.2. The resultant DNA contains 55 molecules ($N_o$) [$^{14}$C]methoxyamine bound per 1000 nucleotides. Incubation is performed at 37° C. either with (curve a) or without (curve b) 10 mM of unlabelled methoxyamine. At the indicated times, the amount of the [$^{14}$C]methoxyamine ($N_t$) still bound to DNA is ascertained in the manner described above, after precipitation in acid.

Figure 6:
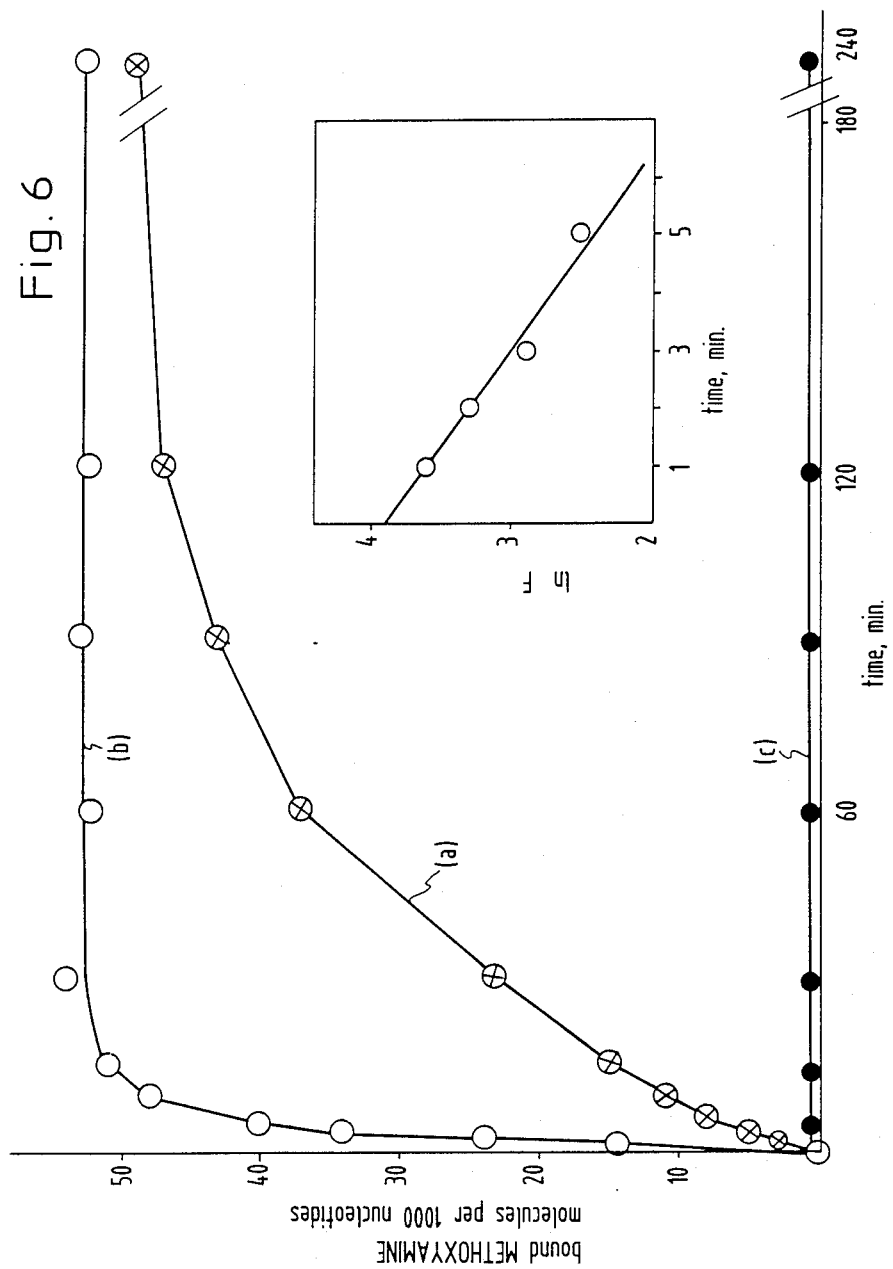

FIG. 6: Reaction of [$^{14}$C]methoxyamine with a synthetic polymer containing apyrimidinic sites The reaction mixtures contain 174 μg/ml of either $(dA)_{230}.(dT, [^3H] dU)_{230}$ treated with uracil-DNA glycosylase or untreated $(dA)_{230}.(dT, dU)_{230}$. Incubation is performed at 37° C. and pH 7.2 with 1 mM (curve a) or 5 mM (curve b) [$^{14}$C]methoxyamine for the polymer with apryimidinic sites and with 5 mM (curve c) for the untreated polymer. At the indicated times the incorporation of the [$^{14}$C]methoxyamine in the polymer is determined in the manner described above.

Figure 7:
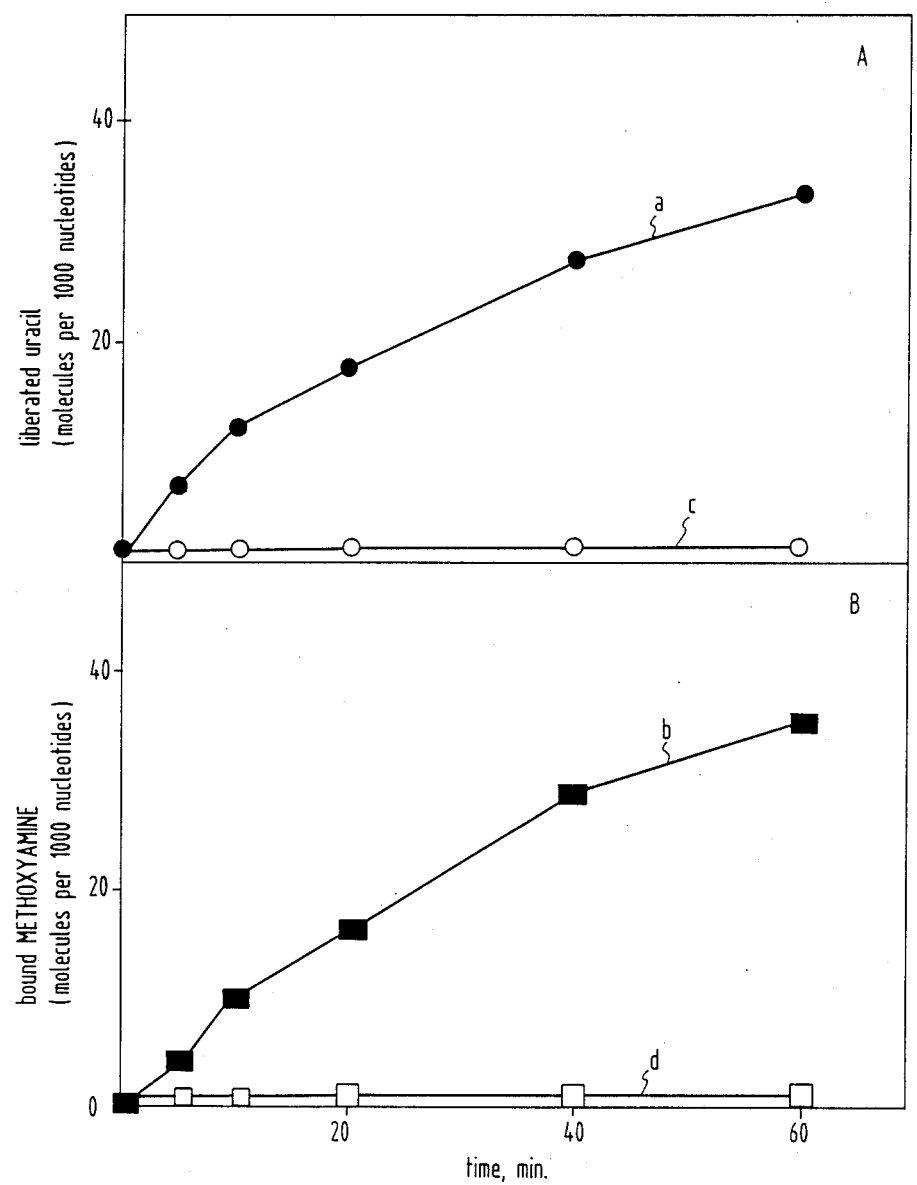

FIG. 7: Reaction of uracil-DNA glycosylase with polydeoxyribonucleotide containing uracil and reaction of the resultant apyrimidinic polymer with /$^{14}$C/methoxyamine; determination of a uracil-DNA-glycosylase FIG. 7A liberated uracil FIG. 7B number of the AP sites

MATERIALS AND METHODS

Materials:

Methoxyamine hydrochloride was obtained from Serva, methyl methane sulfonate from I.C.N. Pharmaceuticals Inc., Escherichia coli DNA was purchased from Worthington, Biochemical Corp. E. coli [$^3$H]DNA (0.29 μCi/μg), [$^{14}$C]methoxyamine hydrochloride (3.13 μCi/μmole) and Omnifluor ® were obtained from New England Nuclear. Insta-Gel ® solution was bought from Packard Instrument Company and glass fiber paper of the type GF/C from Whatman. All other chemicals were analytical grade products.

Uracil-DNA glycosylase was prepared from calf thymus; see M. Talpaert-Borlé et al., J. Biol. Chem., Vol. 254 (1979, pages 6387 to 6391 and Vol. 257 (1982), pages 1208 to 1214.

Uracil-containing polydeoxyribonucleotides $(dA)_{230}.(dT,dU)_{230}$ (dT: dU=9) and $(dA)_{230}.(dT, /^3H/ dU)_{230}$, (150 μCi/umole Uracil; dT: dU=9) were prepared according to the method described in J. Biol. Chem., Vol. 254 (1979), pages 6387 to 6391.

Polydeoxyribonucleotide with apyrimidinic sites

Apyrimidinic sites were introduced in $(dA)_{230}.(dT, [^3H]dU)_{230}$ with dT: dU=9 by uracil-DNA glycosylase according to the method by M. Talpaert-Borlé et al., Eur. J. Biochem., Vol. 124 (1982), pages 435 to 440. The reaction was performed at a concentration of 0.56 mM as total nucleotides with 4.5 enzyme units/ml. After 3 hour incubation at 37° C., the release of [$^3$H]uracil was practically complete. The reaction was stopped and the polydeoxyribonucleotide having about 50 AP sites per 1000 nucleotides was isolated.

Alkylated-depurinated DNA

Unlabelled and tritium labelled E. coli DNA was alkylated with 0.3M methyl methane sulfonate solution and partially depurinated by heating at 50° C. for 6 hours. The resulting DNA's contained approximately one apurinic site per 20 nucleotides; see Can. J. Biochem., Vol. 50 (1972), page 1199 to 1209. Treatment with 0.2 molar caustic soda solution yielded on acid-soluble fraction in an amount of 35%.

Determination of the radioactivity of the acid-soluble fraction

100 μl calf thymus DNA solution (200 μg) in 0.15M NaCl, 15 mM sodium citrate-buffer, pH 7.0 and 220 μl 7.5% perchloric acid solution were added to 10 μl aliquots of the radioactive DNA solutions. After agitation, the mixture was left in ice for 10 minutes. Subsequently, the mixture was centrifuged at 12,000×g for 10 minutes. A portion of the supernatent was made up with water to 0.4 ml, supplemented with 4 ml of Insta-Gel ® solution and placed into a liquid scintillation spectrometer.

Reaction with [$^{14}$C]methoxyamine

The reaction mixture in 0.1M sodium borate buffer, pH 7.2 contained 100 to 200 μg/ml of DNA or synthetic polydeoxyribonucleotides and 3 to 7 mM, preferably 5 mM of [$^{14}$C]methoxyamine (final concentration). The condensation reaction was carried out at 37° C. for 30 minutes.

Determination of the radioactivity of the acid-insoluble fraction

Aliquots of the reaction mixtures were placed on glass fiber discs which were immediately dipped into ice-cold 1M of hydrochloric acid. The free [$^{14}$C]methoxyamine was separated from the acid-insoluble [$^{14}$C]methoxyamine-DNA by washing the glass fiber discs 5 times with 10 ml each of 1M hydrochloric acid for each disc. The discs are then washed 3 times with ethanol. The glass fiber discs are then dried, placed into 4 ml of toluene containing 16 mg of Omnifluor ® and are counted in a liquid scintillation spectrometer. The values for the [$^{14}$C]methoxyamine bound to the acid-insoluble DNA were corrected, since minor amounts of free [$^{14}$C]methoxyamine are retained at the glass fiber discs. This remainder amounted to about 0.05% of the total radioactivity on the glass fiber dics.

Results

1. Determination of apurinic and apyrimidinic sites in DNA;

1.a Reaction of methoxyamine with apurinic sites in alkyllated-depurinated DNA

Alkylated-depurinated DNA contains some groups which bind methoxyamine in a reaction depending on the pH; see FIG. 1. The reaction occurs mainly in the acidic pH range and drops sharply at a pH greater than 8. On the other hand, methoxyamine does not react significantly with untreated DNA; In the pH-range 3 to 6 slight incorporation of methoxyamine takes place. The lowest ratio of the unspecific retention of [$^{14}$C]methoxyamine to the labelling of specific reactive sites in the alkylated-depurinated DNA is at a pH of 7.2.

FIG. 2 shows the amount of [$^{14}$C]methoxyamine taken up untreated and alkylated-depurinated DNAs as a function of the reagent concentration after incubation at 37° C. for 30 minutes and at a pH-value of 7.2.

The incorporation of [$^{14}$C]methoxyamine in untreated DNA remains negligible, even with increasing reagent concentrations. Alkylated-depurinated DNA retains a significant amount of radioactivity, which depends on the reagent concentration. When the final [$^{14}$C]methoxyamine concentration reaches 5 mM, the incorporation curve levels off. It appears that the reactive sites of the alkylated-depurinated DNA are progressively occupied. At a concentration of 5 mM, these sites have taken up 57 molecules of [$^{14}$C]methoxyamine per 1000 nucleotides.

The unspecific retention of the free [$^{14}$C]-methoxyamine on the glass fiber discs used for measuring the incorporation of the radioactive compound in the acid-insoluble DNA increases with increasing reagent concentration. To keep the background radiation at an acceptable level, the lowest concentration of [$^{14}$C]methoxyamine still allowing complete reaction with the AP sites within a reasonable time, i.e. 5 mM of [$^{14}$C]methoxyamine (final concentration) must be used in the assay.

FIG. 3 shows the fixation of [$^{14}$C]methoxyamine by untreated and alkylated-depurinated DNA at two different reagent concentrations as a function of time (incubation at 37° C. and at a pH-value of 7.2). A longer incubation with 5 mM [$^{14}$C]methoxyamine does not produce a significant labelling of the untreated DNA. In contrast to this, the fixation of [$^{14}$C]methoxyamine by alkylated-depurinated DNA increases with time and the reaction speed depends on the reagent concentration. The incorporation curves corresponding to 1 and 5 mM methoxyamine reach the same maximum. This suggests that the reaction of the alkylated-depurinated DNA with methoxyamine goes to completion after a sufficiently long incubation time. The insert of FIG. 3 gives the logarithm of the number of specific reactive sites which have not yet reacted at a methoxyamine concentration of 5 mM, as a function of time. It is a linear realationship. From the inclination of the straight line, the value of the kinetic constant of 34.4 $M^{-1} min^{-1}$ is calculated. The speed of the reaction depends on the temperature. It proceeds 8 times more rapidly at 37° C. than at 0° C. (the values are not shown).

An incubation at 37° C. for 30 minutes with a final methoxyamine concentration of 5 mM which leads to a complete reaction of all reactive sites was chosen for the standard assay. Under these conditions, the amount of bound methoxyamine is proportional to the number of the specific reactive AP sites in the alkylated-depurinated DNA; see FIG. 4.

To detect the stability of the complex after reacting the alkylated-depurinated DNA with [$^{14}$C]methoxyamine, the free labelled reagent was dialyzed away and optionally replaced by 10 mM of unlabelled methoxyamine (final concentration). The results are shown in FIG. 5. In the absence of unlabelled methoxyamine, the radioactive complex is practically stable. In the presence of 10 mM methoxyamine at 37° C. and pH 7.2, the alkylated-depurinated DNA progressively loses the bound [$^{14}$C]methoxyamine. A semi-logarithmic plot of the results yields a straight line, from which a half-life of 42 minutes for the bound [$^{14}$C]methoxyamine can be deduced. This corresponds to a dissociation rate constant of 0.0167 $min^{-1}$. This dissociation rate constant depends on the concentration of the unlabelled methoxyamine (not shown) suggesting that the loss of radioactivity from the alkylated-depurinated DNA results from the substitution of the bound [$^{14}$C]methoxyamine by unlabelled methoxyamine.

Methoxyamine does not cause the alkylated-depurinated DNA to degrade. If alkylated-depurinated [$^3$H]DNA is incubated with the methoxyamine at pH 7.2 and at 37° C., the radioactivity of the acid-soluble fraction does not increase.

Alkylated-depurinated [$^3$H]DNA (100 μg/ml) was incubated at 37° C. with 0.2M sodium hydroxide solution or 5 mM methoxyamine being optionally added. After the times indicated in Table I, the radioactivity of the acid-soluble fraction is determined in the manner described above. The results are shown in Table I.

TABLE I

| Incubation Time, min. | Acid-soluble fraction | | | |
|---|---|---|---|---|
| | NaOH | | Methoxyamine | |
| | − | + | − | + |
| 15 | 1,9 | 36 | 2,2 | 2,6 |
| 30 | — | — | 2,3 | 2,6 |
| 60 | — | — | 2,4 | 2,6 |
| 120 | — | — | 2,7 | 2,7 |

1.b Reaction of methoxyamine with apyrimidinic sites in the synthetic polydeoxyribonucleotide FIG. 6 shows that [$^{14}$C]methoxyamine reacts with the apyrimidinic sites introduced by uracil-DNA glycosylase into a polydeoxyribonucleotide containing uracil. With a reagent concentration of 5 mM, the reaction proceeds rapidly and, after incubation at 37° C. for 30 minutes, reaches a maximum corresponding the saturation of the apyrimidinic sites. As in the case of alkylated-depurinated DNA the reaction with 1 mM methoxyamine (final concentration) requires a longer reaction time than with 5 methoxyamine (final concentration). Moreover, the uracil-containing control polydeoxyribonucleotide does not retain [$^{14}$C]methoxyamine. From the insert of FIG. 6, which gives the logarithm of the unreacted sites at a methoxyamine concentration of 5 mM as a function of time, a kinetic constant of 58.3 $M^{-1} min^{-1}$ can be calculated.

It has been shown by experiments that alkylated DNA containing apurinic sites and a synthetic double-stranded DNA containing apyrimidinic sites fix considerably more [$^{14}$C]methoxyamine than the corresponding control samples, i.e. untreated DNA or the corresponding homologous DNA having no apyrimidinic sites.

Reaction conditions have been detected at which the ratio of specific to unspecific binding of [$^{14}$C]methoxyamine is highest. At a 30 min incubation at 37° C. with 5 mM [$^{14}$C]methoxyamine and at pH 7.2 practically all specific reactive sites (AP sites) of alkylated-depurinated DNA and synthetic DNA containing apyrimidinic sites react with the [$^{14}$C]methoxyamine. Moreover, the reaction rates for the apurinic and apyrimidinic sites, although they are in very different macromolecules, are nearly the same.

Moreover it was found that the reaction of methoxyamine with AP sites is not accompanied by the formation of a strand break so that the bound [$^{14}$C]methoxyamine can be measured by the simple determination of the radioactivity of the acid-insoluble fraction.

The reaction of [$^{14}$C]methoxyamine with specific reactive sites of alkylated-depurinated DNA goes to completion, if the reaction is performed for a sufficiently long time. The reaction has been found to be irreversible. The complex cannot be hydrolyzed at pH 7.2.

Subsequent incubation with unlabelled methoxyamine is, however, associated with a decrease in radioactivity. This is an index of the bound methoxyamine being replaced by the free methoxyamine.

The process according to the invention thus permits the direct determination of apurinic and apyrimidinic sites in DNA, the characterization of substrates for AP-endodeoxyribonucleases, the discovery of new DNA glycosylases and the determination of their activity.

2. Reaction of uracil-DNA glycosylase with polydeoxyribonucleotide containing uracil (dA)$_{230}$.(dT, [$^3$H]dU)$_{230}$, the ratio of dT:dU being 15, was incubated at a concentration of 0.64 mM total nucleotide at 37° C. either with (see curves a and b) or without (see curves c and d) uracil-DNA glycosylase (2.3 units per ml) under the conditions described above.

At the times indicated in FIG. 7, the enzymatic reaction is stopped by the addition of 0.5M KCl (end concentration) and the reaction mixture is heated to 70° C. for 5 minutes. The liberated uracil is calculated from the radioactivity of the acid-soluble fraction (FIG. 7A). The number of the AP sites is calculated from the radioactivity of the acid-insoluble fraction (bound [$^{14}$C]methoxyamine) after incubation under standard conditions (pH 7.2; 37° C.; 5 mM [$^{14}$C]methoxyamine); FIG. 7B.

The comparison of curves a and b reveals that free uracil and apyrimidinic sites reacting with [$^{14}$C]methoxyamine are formed in practically the same amounts. The number of liberated uracil molecules corresponds to the number of bound [$^{14}$C]methoxyamine molecules.

We claim:

1. A process for directly determining apurinic and apyrimidinic sites in DNA, comprising contacting a DNA-sample to be assayed with an effective excess amount of ($^{14}$C) methoxyamine for a time sufficient for said ($^{14}$C) methoxyamine to react with said DNA to form a DNA ($^{14}$C) methoxyamine reaction product at a pH value of from about 6.8 to about 7.4, separating the unreacted ($^{14}$C) methoxyamine from said DNA-($^{14}$C) methoxyamine reaction product in an acidic medium and determining the radioactivity of the DNA-($^{14}$C) methoxyamine reaction product.

2. A process for detecting the presence of DNA glycosylases comprising independently reacting a DNA sample with ($^{14}$C) methoxyamine in the presence of DNA glycosylase in one reaction vessel and in the absence of DNA glycosylase in a second reaction vessel and comparing the radioactivity of the reaction products so obtained.

3. The process according to claim 1 or 2, which comprises reacting said DNA with said ($^{14}$C) methoxyamine at pH 7.2 and at 37° C.

4. A process for directly determining apurinic and apyrimidinic sites in DNA comprising contacting a DNA sample to be assayed with an effective amount of ($^{14}$C)methoxyamine for a time and under conditions sufficient for said ($^{14}$C)methoxyamine to react with said DNA to form a DNA-($^{14}$C)methoxyamine reaction product and determining the radioactivity of said reaction product.

5. The process according to claim 4 wherein the amount of ($^{14}$C)methoxyamine is in excess of the amount of said DNA.

6. The process according to claim 4 wherein the DNA and ($^{14}$C)methoxyamine are reacted at a pH of from about 6.8 to about 7.4 and at 37° C.

7. The process according to claim 6 wherein the DNA and ($^{14}$C)methoxyamine are reacted at pH 7.2 and at 37° C.

* * * * *